United States Patent
Irioka et al.

(10) Patent No.: US 7,431,697 B2
(45) Date of Patent: Oct. 7, 2008

(54) ULTRASONIC PROBE

(75) Inventors: Kazuyoshi Irioka, Sagamihara (JP);
Eiichi Ookawa, Yokohama (JP); Jun Koizumi, Yokohama (JP); Shigeyoshi Hasegawa, Tsukui-gun (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 296 days.

(21) Appl. No.: 10/530,533

(22) PCT Filed: Oct. 16, 2003

(86) PCT No.: PCT/JP03/13225

§ 371 (c)(1),
(2), (4) Date: Apr. 6, 2005

(87) PCT Pub. No.: WO2004/034911

PCT Pub. Date: Apr. 29, 2004

(65) Prior Publication Data

US 2006/0173329 A1    Aug. 3, 2006

(30) Foreign Application Priority Data

Oct. 18, 2002    (JP)    ............... 2002-304912

(51) Int. Cl.
*A61B 8/00*    (2006.01)
(52) U.S. Cl. .................................................. 600/445
(58) Field of Classification Search ............... 600/444, 600/463, 437, 445, 459; 128/662, 660; 250/123.13
See application file for complete search history.

(56) References Cited

U.S. PATENT DOCUMENTS

| 4,141,347 A | * | 2/1979 | Green et al. ............... 600/441 |
| 4,399,703 A | * | 8/1983 | Matzuk ..................... 73/621 |
| 4,531,412 A |   | 7/1985 | Prud'hon et al. |
| 4,690,150 A | * | 9/1987 | Mayo, Jr. ................... 600/440 |
| 4,880,011 A | * | 11/1989 | Imade et al. ............... 600/462 |
| 5,070,879 A | * | 12/1991 | Herres ....................... 600/444 |
| 5,088,495 A | * | 2/1992 | Miyagawa .................. 600/446 |
| 5,152,294 A |   | 10/1992 | Mochizuki et al. |
| 5,427,107 A |   | 6/1995 | Milo et al. |

(Continued)

FOREIGN PATENT DOCUMENTS

EP        0 292 151        11/1988

(Continued)

*Primary Examiner*—Eric F Winakur
*Assistant Examiner*—Lawrence N Laryea
(74) *Attorney, Agent, or Firm*—Hamre, Schumann, Mueller & Larson, P.C.

(57) ABSTRACT

The ultrasonic probe of the present invention includes an ultrasonic element unit for transmitting and receiving ultrasonic waves, an oscillation mechanism for causing oscillation to the ultrasonic element unit and a detector for detecting the oscillation of the ultrasonic element unit. The detector detects the oscillation angle and the oscillation origin of the ultrasonic element unit, and when the oscillation range of the ultrasonic element unit is divided at its oscillation origin into two regions of a positive region and a negative region, the detector detects in which area the ultrasonic element unit is located. In use of the ultrasonic probe, a control of origin return for returning the ultrasonic element unit to its oscillation origin is performed on the basis of the result of the detection by the detector.

7 Claims, 6 Drawing Sheets

U.S. PATENT DOCUMENTS 5,759,155 A    6/1998   Miyagawa
6,551,245 B1 *  4/2003   Irioka et al. ................ 600/444
6,664,900 B1 * 12/2003   Motz et al. ............. 340/870.04

FOREIGN PATENT DOCUMENTS

| EP | 0 432 771 | 6/1991 |
| EP | 0 577 104 | 1/1994 |
| JP | 59-51346 | 3/1984 |
| JP | 64-27538 | 1/1989 |
| JP | 2-116748 | 5/1990 |
| JP | 2-144047 | 6/1990 |
| JP | 3-184532 | 8/1991 |
| JP | 8-98838 | 4/1996 |
| JP | 9-38087 | 2/1997 |
| JP | 2001-170053 | 6/2001 |

* cited by examiner

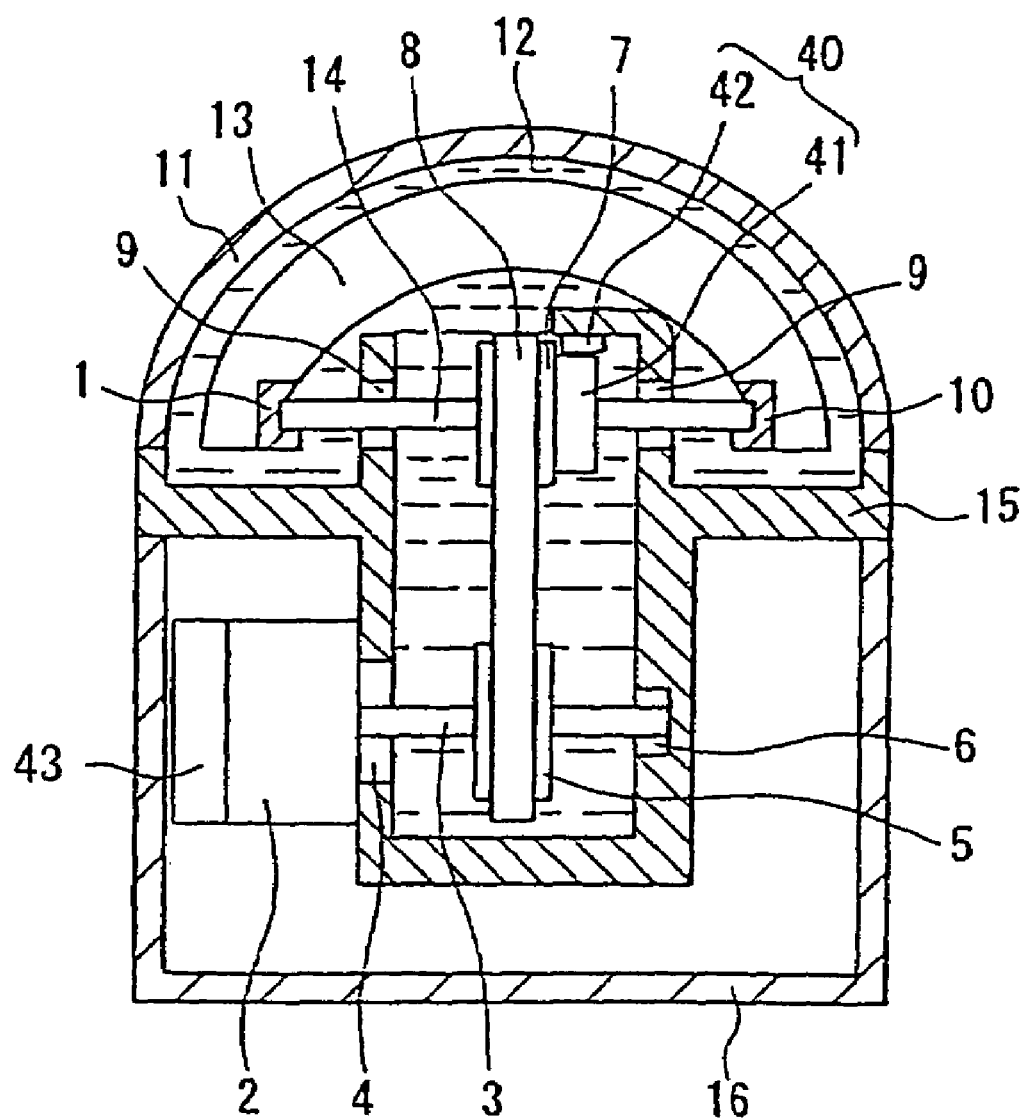
F I G. 5

ULTRASONIC PROBE

TECHNICAL FIELD

The present invention relates to an ultrasonic probe, more specifically, an ultrasonic probe which transmits and receives ultrasonic waves with respect to a subject, changing the surface to be scanned by the mechanical oscillation of an ultrasonic element.

BACKGROUND ART

In a medical field, ultrasonic diagnostic apparatuses are widely used, such an apparatus transmits and receives ultrasonic waves by using an ultrasonic probe with respect to a subject, so that it obtains information about the respective parts of the subject, depending on the acoustic characteristics of the parts. In the ultrasonic diagnostic apparatus, a transducer array as an ultrasonic element for transmitting and receiving ultrasonic waves is used, and this transducer array is oscillated mechanically to change the surface to be scanned with the ultrasonic waves, thereby obtaining three-dimensional information of the subject.

The probe used in such an ultrasonic diagnostic apparatus generally includes an ultrasonic element and an oscillation mechanism for oscillating the ultrasonic element. The oscillation mechanism is configured, for example, by connecting a supporting axis to an output axis of a motor via a gear and connecting to this supporting axis a holder that holds the ultrasonic element. In the oscillation mechanism, when the motor is driven, the rotary power is transmitted to the supporting axis via the gear so as to cause rotation to the supporting axis, thereby the ultrasonic element rotates with the holder, in synchronization with the movement of the supporting axis. By reversing the rotating direction of the motor at predetermined time intervals so as to reverse the rotating direction of the ultrasonic element, oscillation of the ultrasonic element is provided.

Furthermore, the oscillation mechanism provided with an angle detector to detect oscillation angle of the ultrasonic element has been proposed (for example, see JP3(1991)-184532A). FIG. 7 is a perspective view showing the structure of the angle detector which composes a conventional ultrasonic probe. The angle detector 70 is composed of a slit plate 72 which rotates together with the supporting axis 71 and has plural slits arranged concentrically about the rotating axis, and an optical counter 73 arranged pinching the slit plate 72. The optical counter 73 is divided at the slit plate 72 into two parts: one is for emitting light and the other is for receiving light that has passed through the slits. Based on the number of the light reception counts, the rotation angle of the slit plate 72, that is, the rotation angle of the supporting axis 71 is detected. By detecting the rotation angle of the supporting axis as above, the rotation angle (the oscillation angle) of the ultrasonic element which rotates together with the supporting axis can be detected as well.

In the conventional ultrasonic probe, however, the detector detects only the number of light reception counts, thus it has been impossible to detect accurately an oscillation origin or the position of the ultrasonic element at the time of turning on a switch with respect to the ultrasonic probe. This has caused a problem that control of origin return of the ultrasonic element would be complicated, thus delaying a time for the origin return.

DISCLOSURE OF THE INVENTION

The object of the present invention is to provide an ultrasonic probe which can control the origin return of an ultrasonic element easily and swiftly.

In order to attain the above-mentioned object, the ultrasonic probe of the present invention includes an ultrasonic element unit for transmitting and receiving ultrasonic waves, an oscillation mechanism for oscillating the ultrasonic element unit and a detector for detecting the oscillation of the ultrasonic element unit, wherein the detector detects the oscillation angle and the oscillation origin of the ultrasonic element unit, and when the oscillation range of the ultrasonic element unit is divided at the oscillation origin into a positive region and a negative region, the detector detects in which region the ultrasonic element unit is located, and on the basis of the result of the detection by the detector, origin return control for returning the ultrasonic element unit to its oscillation origin is performed.

BRIEF DESCRIPTION OF DRAWINGS

FIG. 5 is a cross-sectional view of an example of an ultrasonic probe according to Embodiment 2 of the present invention.

BEST MODE FOR CARRYING OUT THE INVENTION

Figure 1:
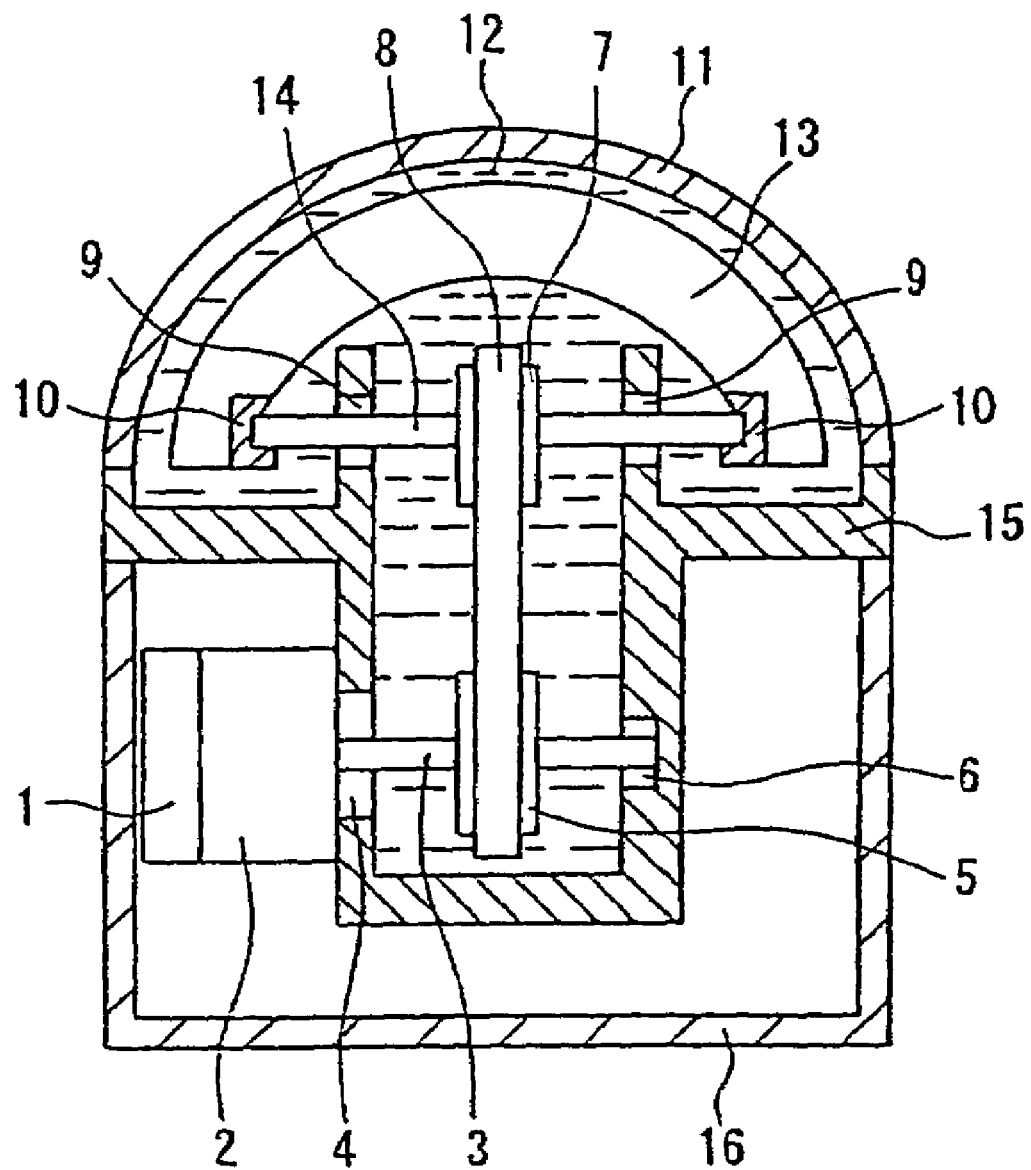
FIG. 1 is a cross-sectional view of an example of an ultrasonic probe according to Embodiment 1 of the present invention.

The ultrasonic probe of the present invention includes a detector for detecting the oscillation angle and the oscillation origin of an ultrasonic element unit. In addition, when the oscillation range of the ultrasonic element unit is divided at the oscillation origin into two regions of a positive region and a negative region, the detector detects in which area the ultrasonic element unit is located. In using the ultrasonic probe, origin return control for returning the ultrasonic element unit to its oscillation origin is performed on the basis of the result of the detection by the detector. More specifically, information about the position and the oscillation origin of the ultrasonic element unit is provided to a control mechanism of the ultrasonic diagnostic apparatus at the time of the origin return control when turning on the power, and the control of origin return can be performed on the basis of this information. Thereby, the return operation can be carried out easily and swiftly.

In the ultrasonic probe, the detector can be structured for outputting at least a single-phase rotary encoder pulse signal as an angle signal, detecting the oscillation angle on the basis of the angle signal, outputting an origin-return signal that shows different logic levels depending on whether the ultrasonic element unit is located in the positive region or the negative region, and detecting the oscillation origin on the basis of the changing point of the logic level of the origin-return signal (that is, a rising edge or a falling edge).

Moreover, in the ultrasonic probe, the detector can include: a slit plate which oscillates together with the ultrasonic element unit and has a first slit formed in an arc-shape from a position corresponding to the oscillation origin to a position at least corresponding to the end of the positive region or the negative region about the oscillation axis of the slit plate; a light source for radiating light to the slit plate; and a first photodetector which detects the light passed through the first slit, converts it into an electric signal and outputs the origin-return signal.

Furthermore, in the ultrasonic probe, the detector can include: a slit plate which oscillates together with the ultrasonic element unit and has plural second slits arranged at a predetermined pitch concentrically or in an arc-shape about the oscillation axis; a light source for radiating light to the slit plate and a second photodetector which detects the light emitted from the light source and passed through the second slits; converts it into an electric signal and outputs the angle signal.

Here, the first slit and the second slits are preferably formed to the same slit plate.

Still further, in the ultrasonic probe, the detector can include: a magnetic dram which oscillates together with the ultrasonic element unit and has plural magnetic patterns arranged at a predetermined pitch concentrically or in an arc-shape about the oscillation axis; and a magnetoresistive element which detects a magnetic pattern of the magnetic dram, converts it into an electric signal and outputs an angle signal.

Here, the magnetic dram is preferably provided on the oscillation axis which is fixed directly to the ultrasonic element unit.

The following is a description of preferred embodiments of the present invention, with reference to the accompanying drawings.

Embodiment 1

FIG. 1 is a cross-sectional view showing an example of the ultrasonic probe according to Embodiment 1 of the present invention. In the ultrasonic probe, a medium chamber is formed by connecting a window 11 to a frame 15. The medium chamber is filled with a degassed acoustical coupling medium 12. In the medium chamber, an ultrasonic element unit 13 formed by aligning plural oscillators is contained. The ultrasonic element unit 13 is fixed to an oscillation axis 14 by an oscillation axis holder 10, and the oscillation axis 14 is supported rotatably by a bearing 9 provided to the frame 15.

By fixing the oscillation axis 14 directly to the ultrasonic element unit 13 as mentioned above, the radius of the oscillation can be decreased, therefore, the size of the window 11 can be decreased relatively to the oscillation scanning angle of the ultrasonic element unit 13, and the moment of inertia with respect to the oscillation axis 14 can be reduced, thus realizing the reduction of the torque of a motor.

Further in the ultrasonic probe, an oscillation mechanism for oscillating the ultrasonic element unit 13 is contained. The oscillation mechanism includes a motor as a driving force and a oscillation transmitting mechanism for conveying the rotation driving force of the motor 2 to the ultrasonic element unit. The oscillation transmitting mechanism includes a driving pulley 5 attached to an output axis 3 of the motor, a driven pulley 7 attached to the oscillation axis and a transmission belt 8 bridged between these pulleys. The motor 2 is fixed to the frame 15 via an oil seal 4 which prevents the acoustical coupling medium 12 from entering into the motor. The output axis 3 of the motor is supported by a bearing 6 provided to the frame 15, and the motor 2 is covered with a cabinet 16 which is connected to the frame 15.

In the above oscillation mechanism, when the motor 2 is driven, the driving pulley provided with the output axis 3 rotates. The rotation of the driving pulley 5 is transmitted to the driven pulley 7 via the transmission belt 8, thus the driven pulley 7 rotates. The oscillation axis 14 rotates in synchronization with the rotation of the driven pulley 7, subsequently the ultrasonic element unit 13 rotates in synchronization with the rotation of the oscillation axis 14. By reversing the rotating direction of the motor at a predetermined time interval, the rotating direction of the ultrasonic element is reversed as well, thus realizing the oscillation of the ultrasonic element.

Moreover, a detector 1 for detecting the oscillation of the ultrasonic element unit 13 is contained in the ultrasonic probe. The detector 1 is configured for enabling detection of the oscillation angle and the oscillation origin of the ultrasonic element unit 13. In addition, the detector 1 is configured so that it can detect, when the oscillation range of the ultrasonic element unit is divided into two regions (hereinafter, these regions are called a positive region and a negative region, respectively) at the position of the ultrasonic element unit 13 (that is, the oscillation origin), in which region of the positive region or the negative region the ultrasonic element unit 13 is located.

The detector can also be attached to the oscillation axis so as to detect the oscillation of the ultrasonic element unit directly. Alternatively, the detector can be structured to detect the movement of a member which oscillates (rotates) together with the ultrasonic element unit (for example, such as the output axis of the motor) so as to detect the oscillation of the ultrasonic element unit indirectly.

In the ultrasonic probe illustrated in FIG. 1, for example, the detector 1 is attached to the motor 2, and configured to detect the oscillation of the motor. As mentioned above, since the oscillation of the ultrasonic element unit is in synchronization with the rotation of the motor, the rotation of the ultrasonic element unit can be detected by detecting the rotation of the motor.

Figure 2:
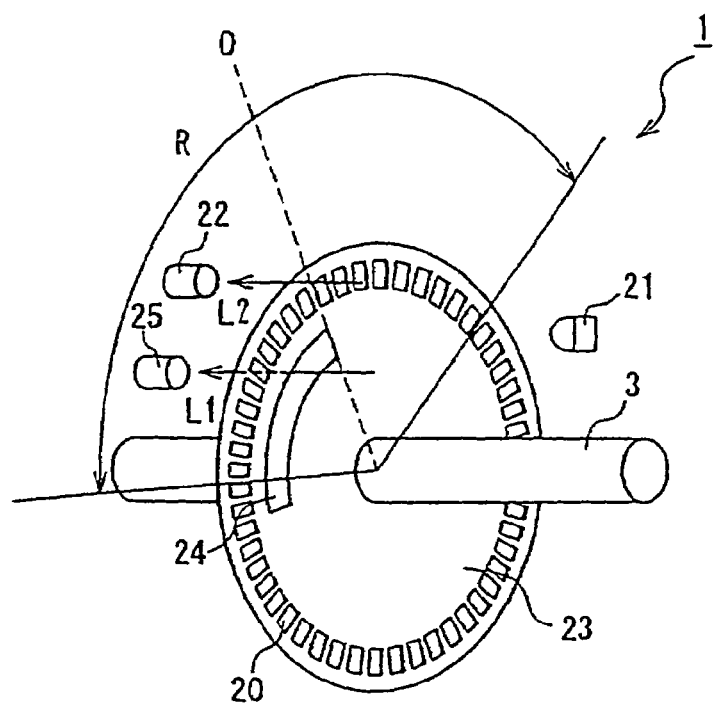
FIG. 2 is a schematic view of an example of a detector composing the ultrasonic probe according to Embodiment 1.

FIG. 2 is a schematic view showing an example of the configuration of the detector 1. The detector 1 is structured as an optical incremental-type rotary encoder. In the detector 1, a slit plate 13 is attached to the output axis 3 of the motor so that the slit plate can rotate together. In the slit plate 23, a first slit 24 used for detecting the position and the oscillation origin of the ultrasonic element unit and second slits 20 used for detecting the oscillation angle are formed concentrically about the rotation axis of the slit plate. Light from a light source 21 is directed to the second slit 20, and the amount of light L2 passed through the second slits 20 is detected by a second photoreceptor 22. The light signal detected by the second photoreceptor 22 is converted into an electric signal and subsequently output as an angle signal. The light from the light source 21 is also directed to the first slit 24, and the amount of light L1 passed through the first slit 24 is detected by a first photoreceptor 25. And the light signal detected by the first photoreceptor 25 is converted into an electric signal and subsequently output as an origin-return signal.

The slits formed in the slit plate will be described below in detail with reference to FIG. 2. In FIG. 2, O denotes the position that corresponds to the oscillation origin of the ultrasonic element unit, where the ultrasonic element unit overlaps the photodetector. The sign of R denotes a region that corresponds to the oscillation range of the ultrasonic element unit, in which the ultrasonic element unit can pass in front of the photodetector during its oscillation.

The first slit 24 is for detecting the position and the oscillation origin of the ultrasonic element unit, and it is formed circularly about the rotation axis of the slit plate 23. As illustrated in FIG. 2, the first slit 24 is formed as an opening so that one end thereof is aligned with the position (O) that corresponds to the oscillation origin, while the other end is aligned with one end of the region (R) that corresponds to the oscillation range of the ultrasonic element unit. That is, when the region (R) which corresponds to the oscillation range of the ultrasonic element unit is divided into two parts by the position (O) corresponding to the oscillation origin, the first slit is formed in the whole range of one of the above-mentioned parts, but not formed in the other part.

The plural second slits 20 for angle detection are formed at the periphery of the slit plate 23 at a predetermined pitch. Though, there is no specific limitation, it is preferable that the number of the second slits is larger (that is, the shorter the pitch is), because the resolution for detecting the oscillation angle becomes higher. Alternatively, as additional slits for angle detection, plural slits can be formed, and the slits are arranged concentrically at the same pitch (P) as that of the second slits with a phase difference of P/4 (hereinafter, these additional slits may be called 'third slits').

Figure 3:
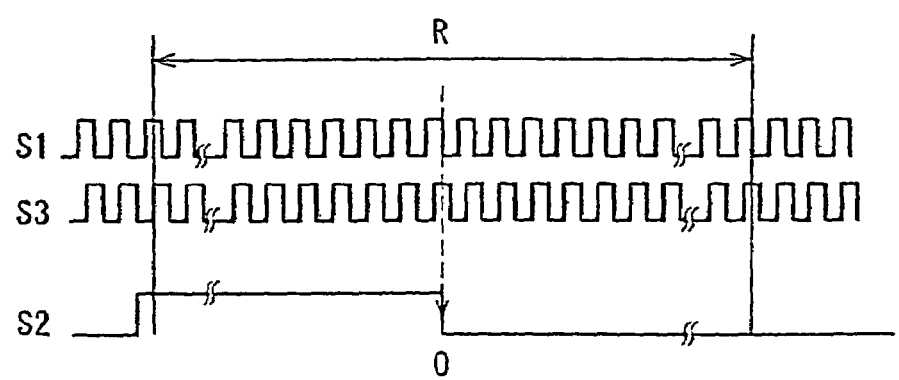
FIG. 3 is a timing chart of an example of an angle signal and a origin-return signal which are obtained by the detector.

The operation by the detector 1 for detecting the oscillation is described below with reference to FIG. 3. FIG. 3 is a timing chart of an example of the detection signal obtained by the detector. In FIG. 3, the detection signals S1 and S3 are obtained respectively with respect to the second slits and the third slits and used as angle signals. The detection signal S2 is obtained with respect to the first slit 24, and used as an origin-return signal.

The position of the ultrasonic element unit can be detected by detecting the light passed through the first slit 24. As mentioned above, the first slit 24 is formed so that when the region (R) corresponding to the oscillation range of the ultrasonic element unit is divided into two regions at the position (O) that corresponds to the oscillation origin, the opening is formed in the whole range of one of the regions, but no opening is formed in the other region. Therefore, when the ultrasonic element unit 13 is located in one of the parts of the oscillation range (for example, in the positive region) which is one of the oscillation regions is divided at the oscillation origin, the first slit 24 is positioned between the light source and the first photodetector, thus the light passed through the first slit 24 will be detected. Alternatively, when the ultrasonic element unit 13 is located in the other region of the oscillation range (for example, in the positive region), the first slit 24 is not be positioned between the light source and the first photodetector, thus the light passed through the first slit 24 is not detected. Thereby, it is possible to decide, by detecting whether light passing through the first slit 24, in which part of the right or left region with respect to the oscillation origin (in other words, the positive area or the negative area) the ultrasonic element unit is located.

In addition, the oscillation origin is detected from the signal obtained by detecting the light passed through the first slit 24 (that is, the origin-return signal). The detection of the oscillation origin is described with reference to FIG. 3. When the output axis of the motor rotates and the slit plate 23 rotates together with the output axis, the origin-return signal which is obtained by the first slit 24 becomes a binary signal as illustrated as, for example, S2 in FIG. 3. Each logic level of the signal for origin return corresponds to the light passed through the first slit: logically high level is output when the light passed through the first slit is detected, and logically low level is output when the light passed through the first slit is not substantially detected. A changing point (O) where the origin-return signal changes from the logically high level to the logically low level is located at only one position in the region (R) which corresponds to the oscillation range, and this changing point corresponds to oscillation origin. Thereby, the oscillation origin can be detected by detecting the changing point from the logically high level to the logically low level.

Detection of the oscillation angle of the ultrasonic element unit is carried out by detecting the light passing through the second slits 20. When the slit plate 23 rotates, the signal (the angle signal) obtained by the second slits 20 becomes, for example, a binary pulse signal as illustrated as S1 in FIG. 3. The each logic level of the angle signal depends on the detection of the light passed through the second slits. The number of pulses corresponds to the number of the second slits passed in front of the second photoreceptor within a predetermined time period. Therefore, the oscillation angle can be obtained by counting the number of these pulses.

In a case where the third slits are provided, when the slit plate 23 rotates, the signal (the angle signal) obtained by the third slits becomes, for example, a binary pulse signal having a phase difference of T/4 with respect to the signal (S1) obtained by the second slits 20 as illustrated as S3 in FIG. 3. Thereby, a double-phase pulse can be obtained as an angle signal by providing the third slits, thus improving further angle-detecting resolution.

For a case of an encoder of 500 pulses (that is, having 500 slits), when the angle signal is a single-phase pulse, an angle-detecting resolution will be 0.36, and the resolution will be 0.18 when the angle signal is a double-phase pulse. Moreover, in a case where the angle signal is a single-phase pulse, stop control can be performed with an accuracy of T/2 for the frequency (T) of the pulse or with a higher accuracy of T/4 when the angle signal is a double-phase pulse.

In the above description, the example of forming a slit in an opaque plate is illustrated, but the present invention is not limited to the example. Similar functions can be obtained by forming black grids on a transparent plate such as a glass plate. The present embodiment exemplified a transmission-type optical rotary encoder as the detector, but a reflection-type optical rotary encoder can provide similar functions.

Figure 4:
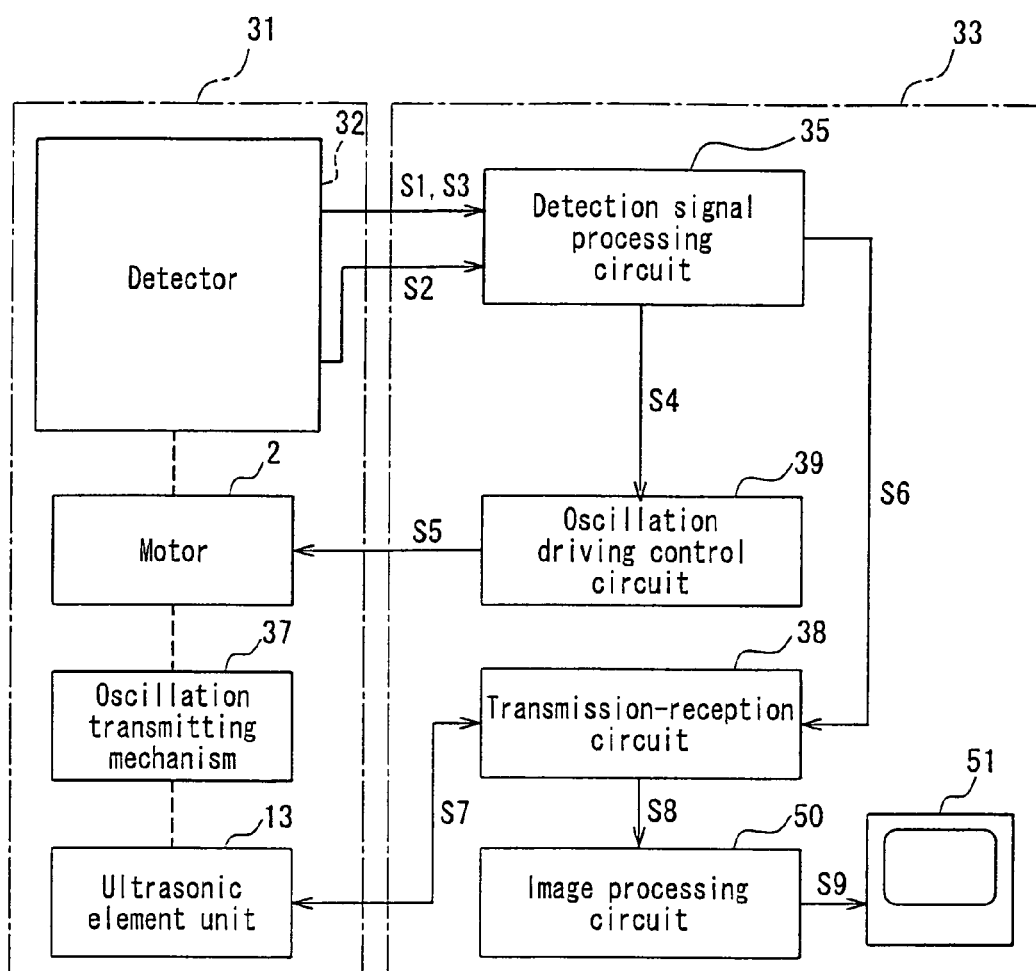
FIG. 4 is a block diagram of a circuit structure of an ultrasonic tomographic diagnostic apparatus using the ultrasonic probe.

Ultrasonic diagnostics using the above-mentioned ultrasonic probe will be described below. FIG. 4 is a block diagram showing an example of a circuit structure of an ultrasonic diagnostic apparatus using the ultrasonic probe. In FIG. 4, 31 denotes the structure inside the ultrasonic probe, and 33 illustrates the structure inside the ultrasonic diagnostic apparatus.

The angle signals S1, S3, and the origin-return signal S2 are produced at the detector 32 and these signals are transmitted to a detection signal processing circuit 35 of the diagnostic apparatus 33. On the basis of the angle signals S1, S3 and the origin-return signal S2 produced at the detector 32, the detection signal processing circuit 35 produces a control signal S4 for performing the oscillation control and the control for origin return of the ultrasonic element unit, and transmits the control signal S4 to an oscillation driving control circuit 39. The oscillation driving control circuit 39 produces a driving signal S5 and transmits the signal to a motor 2 in the ultrasonic probe for the purpose of drive-control. The rotary driving force of the motor is transmitted to the ultrasonic element unit 13 by an oscillation transmitting mechanism 37, thereby the oscillation operation and the control for origin return of the ultrasonic element unit 13 are performed.

The angle detection signal processing circuit 35 transmits a control signal S6 to a transmission-reception circuit 38, and the transmission-reception circuit 38 sends a driving signal S7 to the ultrasonic element unit 13. This signal is converted at the ultrasonic element unit 13 into ultrasonic waves, and transmitted to a subject. The ultrasonic wave is reflected by the subject, and a part of the reflected wave is received by the ultrasonic element unit, converted into an electric signal S8 (received signal), and sent to the transmission-reception circuit. Subsequently, the signal S8 is converted into an image signal S9 by an image processing circuit 50, thereby a tomographic image of the subject corresponding to the image signal S9, is displayed on a monitor 51.

As mentioned above, according to the ultrasonic probe of the present embodiment, it is possible to detect, by using the detector, the position of the ultrasonic element unit as well as its oscillation angle and oscillation origin of the ultrasonic element unit. Therefore, for example, for the origin return control at the time of turning on the power, information about the position and the oscillation origin of the ultrasonic element unit is provided as a origin-return signal S2 to a control mechanism of the ultrasonic diagnostic apparatus, and the origin return control can be performed on the basis of the information. Thereby, the return operation can be performed easily and swiftly.

Furthermore, the present embodiment has an advantage that both of the oscillation angle and the oscillation origin of the ultrasonic element unit can be detected easily by one detector.

Embodiment 2

FIG. 5 is a cross-sectional view showing an example of the structure of the ultrasonic probe according to Embodiment 2 of the present invention. A detector in the present invention is composed of an oscillation angle detector and an oscillation origin detector which are separated from each other. In FIG. 5, the same parts as in FIG. 1 are assigned with the same reference numerals, and the description about the parts are omitted.

An origin detector 43 is for detecting the position and the oscillation origin of the ultrasonic element unit. This is structured as an optical rotary encoder, and attached to an output axis of a motor 2. The origin detector 43 can have the same structure as the detector illustrated in FIG. 2, except that the second slits 20 and the second photoreceptor 22 are omitted. The detection operation is substantially the same as that of the first slits in Embodiment 1.

Figure 6:
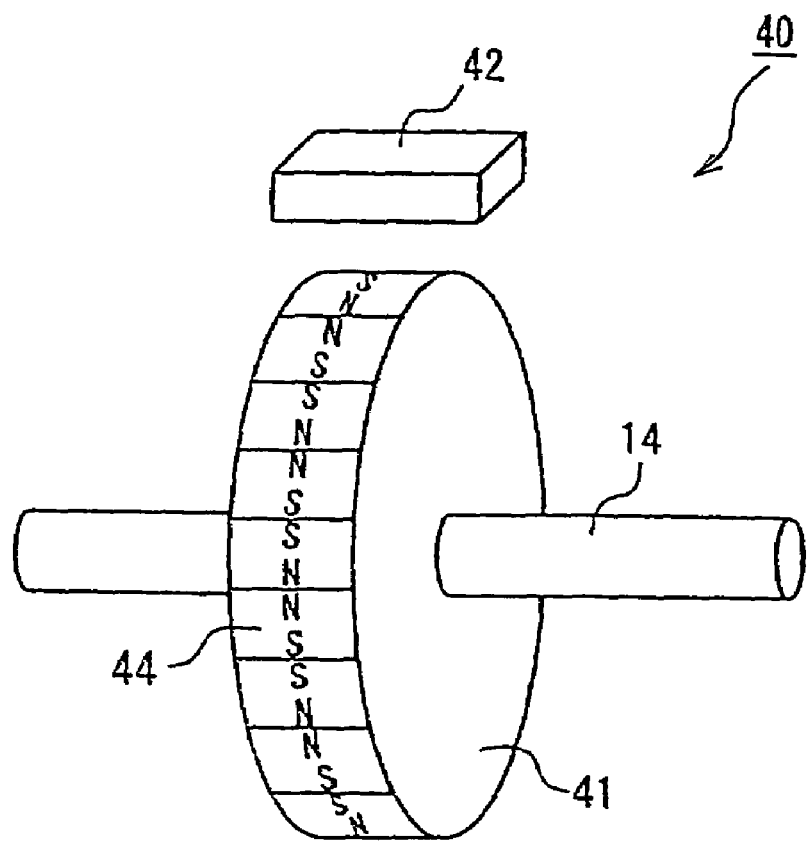
FIG. 6 is a schematic view of an example of a detector composing the ultrasonic probe according to Embodiment 2.
Figure 7:
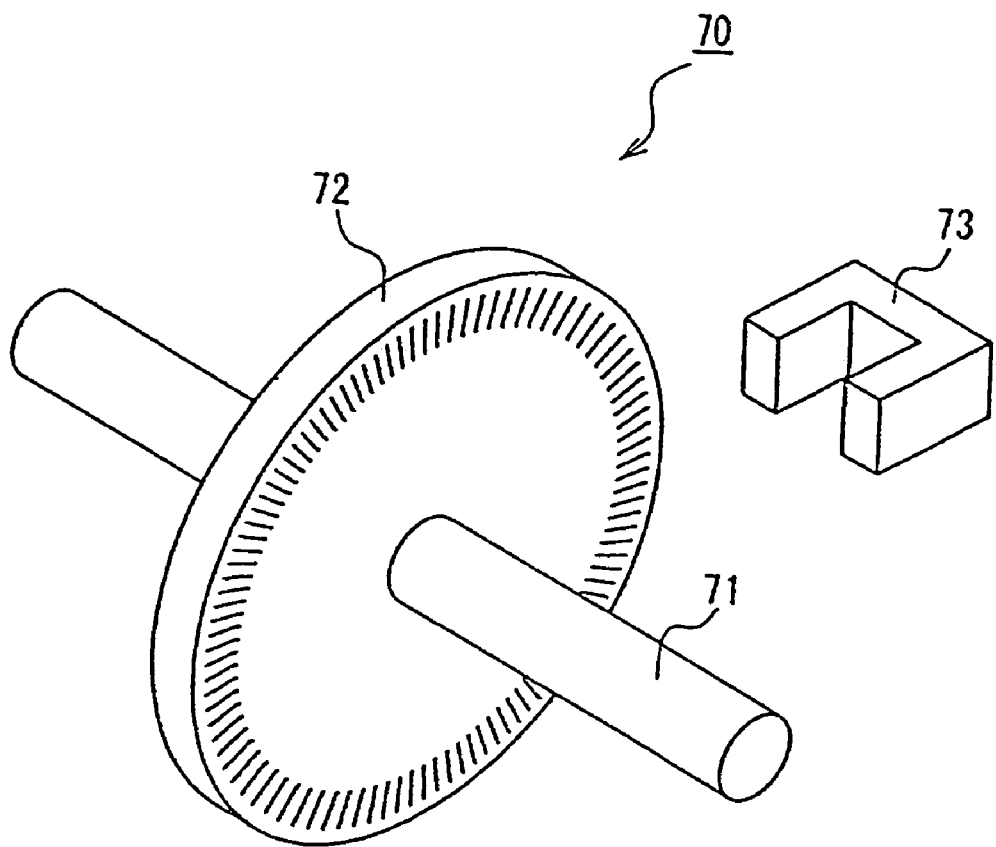
FIG. 7 is a schematic view of a detector composing a conventional ultrasonic probe.

An oscillation angle detector 40 is for detecting the oscillation angle of the ultrasonic element unit, and it can be structured as a magnetic rotary encoder. FIG. 6 is a detailed configuration of the oscillation detector 40. This oscillation detector 40 includes a magnetic dram 41 attached to an oscillation axis 14 and a magnetoresistive element 42 attached to a frame 15. A magnetic pattern 44 is formed on the surface 43 of the magnetic dram 41 at a predetermined pitch. This magnetic pattern 44 is detected by using the magnetoresistive element 42, and the obtained detection signal is used for detecting the oscillation angle.

In the present embodiment, the oscillation angle is detected by the oscillation angle detector 40, and the position and the oscillation origin of the ultrasonic element unit are detected by the origin detector 43. Therefore, at the time of the origin return control, information about the position and the oscillation origin of the ultrasonic element unit is provided to a control mechanism of the ultrasonic diagnostic apparatus as an origin-return signal. Thereby, the return operation can be carried out easily and swiftly.

Moreover, in the present embodiment, since the oscillation angle detector 40 is structured by using the magnetic rotary encoder, the oscillation angle can be detected even in the acoustical coupling medium 12. Therefore, the angle detector can be arranged in larger area in the ultrasonic probe.

Furthermore, unlike Embodiment 1, since the angle detector 40 in the present embodiment provided to the oscillation axis 14 that is directly fixed to the ultrasonic element unit 13, the oscillation angle of the ultrasonic element unit 13 can be detected directly, not via the oscillation transmitting mechanism. Thereby, influences of a transmission error such as a back lash by the oscillation transmission mechanism can be prevented, thus realizing a high-accuracy detection of the oscillation angle of the ultrasonic element unit 13.

INDUSTRIAL APPLICABILITY

As described above, the ultrasonic probe of the present invention can detect the position and the oscillation origin of the ultrasonic element unit when turning on the power, for example. Thus, control of the origin return of the ultrasonic element unit can be performed easily, thereby the origin return can be performed swiftly. The ultrasonic probe is particularly useful for an ultrasonic diagnostic apparatus which can obtain information about the interior of a living organism by transmitting and receiving ultrasonic waves with respect to the living organism.

The invention claimed is:

1. An ultrasonic probe comprising:
   an ultrasonic element unit for transmitting and receiving ultrasonic waves;
   an oscillation mechanism for causing oscillation to the ultrasonic element unit; and
   a detector for detecting oscillation of the ultrasonic element unit,
   wherein the detector detects an oscillation angle and an oscillation origin of the ultrasonic element unit, and in a state where an oscillation range of the ultrasonic element unit is divided at the oscillation origin into two regions of a positive region and a negative region, the detector outputs an origin-return signal that shows different logic levels depending on whether the ultrasonic element unit is located in the positive region or the negative region, and
   a control to return the ultrasonic element unit to the oscillation origin on the basis of the origin-return signal.

2. The ultrasonic probe according to claim 1, wherein the detector outputs at least a single-phase rotary encoder pulse signal as an angle signal, and detects the oscillation angle on the basis of the angle signal, and
   the detector detects the oscillation origin on the basis of the changing point of the logic level of the origin-return signal.

3. The ultrasonic probe according to claim 2, wherein the detector comprises:
   a slit plate which oscillates together with the ultrasonic element unit and has a first slit formed in an arc-shape about the oscillation axis from a position corresponding to the oscillation origin to at least a position corresponding to the end of the positive region or the negative region;
   a light source for radiating light to the slit plate; and
   a first photodetector which detects the light emitted from the light source and passed through the first slit, converts the detected light into an electric signal and outputs an origin-return signal.

4. The ultrasonic probe according to claim 3, wherein the detector comprises:
- a slit plate which oscillates together with the ultrasonic element unit and has plural second slits aligned at a predetermined pitch concentrically or in an arc-shape about the oscillation axis;
- a light source for radiating light to the slit plate; and
- a second photodetector which detects the light emitted from the light source and passed through the second slits, converts the detected light into an electric signal and outputs an angle signal.

5. The ultrasonic probe according to claim 4, wherein the first slit and the second slits are formed on the same slit plate.

6. The ultrasonic probe according to claim 3, wherein the detector comprises:
- a magnetic dram which oscillates together with the ultrasonic element unit and has plural magnetic patterns aligned at a predetermined pitch concentrically or in an arc-shape about the oscillation axis; and
- a magnetoresistive element which detects a magnetic pattern of the magnetic dram converts into an electric signal and outputs an angle signal.

7. The ultrasonic probe according to claim 6, wherein the magnetic dram is provided on the oscillation axis which is fixed directly to the ultrasonic element unit.

* * * * *